United States Patent [19]

Thakur et al.

[11] Patent Number: 5,391,361
[45] Date of Patent: Feb. 21, 1995

[54] CONDENSATE SEPARATOR

[75] Inventors: Bhabesh K. Thakur, West Henrietta; Leonard L. Hallings, East Rochester, both of N.Y.

[73] Assignee: MDT Corporation, Torrance, Calif.

[21] Appl. No.: 644,449

[22] Filed: Jan. 23, 1991

[51] Int. Cl.[6] .................................................. A61L 2/20
[52] U.S. Cl. .................................. 422/295; 137/171; 137/203; 422/26
[58] Field of Search .................. 55/319; 137/171, 202; 422/26, 295; 210/767, 774, 800, 804, 806, 808, 120, 137, 175, 180, 181, 182, 188, 251, 295, 299, 300, 301, 310, 322

[56] References Cited

U.S. PATENT DOCUMENTS

| | | | |
|---|---|---|---|
| 2,838,131 | 6/1958 | Peterson | 55/319 |
| 4,004,604 | 1/1977 | Deinlein-Kalb . | |
| 4,164,538 | 8/1979 | Young et al. | 422/26 |
| 4,302,227 | 11/1981 | Miller . | |
| 4,338,096 | 7/1982 | Mayes | 422/110 X |
| 4,443,354 | 4/1984 | Eian | 55/387 X |
| 4,447,394 | 5/1984 | Krouthén | 422/33 X |
| 4,764,351 | 8/1988 | Hennebert et al. . | |
| 5,027,642 | 7/1991 | Wen et al. | 55/319 X |

OTHER PUBLICATIONS

"The Condensed Chemical Dictionary," 8th Ed., Gessner G. Hawley, Van Nortrand Reinhold Company, pp. 399,400 & 564, Aug. 1976.

Primary Examiner—Timothy M. McMahon
Attorney, Agent, or Firm—Trask, Britt & Rossa

[57] ABSTRACT

A condensate separator includes a vertically oriented cylindrical body with an inlet at its bottom and an outlet at its top. The cross-section of the body is at least an order of magnitude larger than the cross-section of the inlet.

7 Claims, 2 Drawing Sheets

CONDENSATE SEPARATOR

BACKGROUND OF THE INVENTION

1. Field

This invention relates to the handling of saturated vapor streams. It is particularly directed to a condensate separator system for use in connection with chemical vapor sterilizers.

2. State of the Art

Chemical vapor sterilizers produce a quantity of used sterilant which cannot under modern constraints be directly discharged. Following a sterilizing procedure, used chemical sterilant is commonly condensed and collected in a reservoir for eventual safe disposal. The chemical vapor is typically passed through cooling coils to bring its temperature to below the vaporization temperature (e.g., 60°-70° C.) of its constituents. The remaining vapor stream may be discharged to the atmosphere. This stream may be discharged through the accumulated liquid sterilant prior to being vented to the atmosphere. Chemical sterilants often include water as a major constituent, and the vapor stream leaving the sterilizer may be saturated with respect to water. The vent stream following condensation is typically saturated, and includes condensed droplets of water and chemical sterilant. Current safety standards require that the vent stream pass through a chemical filter to reduce its chemical sterilant composition to trace amounts. Entrained moisture and condensate interfere with this process and shorten the useful life of a chemical filter. Entrained moisture and condensate can also cause a water hammer effect in the piping leading to the filter. It would be desirable to remove these constituents from the vent stream so that relatively dry vapor reaches the filter. Unfortunately, conventional steam traps and other well-known condensate collectors are either ineffective or unacceptably complex for this purpose.

Certain modern sterilizers may be operated optionally with steam or chemical sterilant cycles. Accordingly, the waste reservoir may at any given time contain a proportion of water ranging up to 100 percent. Similarly, the vent stream from a steam cycle may contain droplets of water only. It is not economically practical to provide separate venting systems for vent streams containing insignificant quantities of chemical sterilants. Accordingly, the chemical filters in such systems are exposed to entrained moisture following each sterilization cycle.

Steam trap devices of various types are used for removing condensate at saturated steam temperatures. These devices are not effective for use at temperatures close to ambient. The vent streams of a chemical sterilizer are typically much closer to ambient temperature (e.g. 60° C.) than to saturated steam temperatures (e.g. 130° C.).

U.S. Pat. No. 4,004,604 discloses a method and apparatus for drawing condensate from a steam-containing system. The apparatus is configured as a valve with a cascade section responsive to changes in the physical nature of medium in the section, thereby permitting liquid flow but blocking vapor flow.

U.S. Pat. No. 4,302,227 discloses a complex baffled moisture separator.

U.S. Pat. Nos. 4,447,394 and 4,764,351 describe sterilization methods utilizing formaldehyde, but lacking a condensate separator for the vent stream.

There remains a need for a low-cost, effective means for removing moisture and condensate from the vent stream of a chemical sterilizer at close to ambient temperature and pressure conditions.

SUMMARY OF THE INVENTION

The present invention provides a simple low-cost system for removing entrained moisture and condensate from a flowing saturated vapor stream. It finds particular application for removing toxic chemical vapors from vapor streams destined for discharge to the atmosphere, particularly when these streams are at temperature and pressure conditions close to ambient, making conventional expedients relatively ineffective. The claimed condensate separator system manipulates the velocity of a moving vapor stream to permit settling of droplets. Those droplets are collected and returned to their source or origin (the waste reservoir) without the need for additional auxiliary devices or piping.

The invention is useful in sterilizers of the type in which a vent stream of chemical vapor sterilant is passed through a conduit (which may comprise a number of segments interconnecting coils, tanks and other components) of a venting system. The vent stream is initiated following a sterilization cycle and involves passing the sterilant through condensing coils to recover liquid sterilant and discharging the remaining vapor stream to the atmosphere. Droplets of moisture and condensed sterilant are removed from the vent stream by the improvement of this invention which comprises a chamber with an inlet and an outlet positioned in circuit with the conduit. The inlet is positioned at a lower vertical location than is the outlet so that the vent stream enters the inlet and flows upward towards the outlet. The internal configuration (cross-section and height) is selected to provide a sufficiently lower vent stream velocity within the chamber to permit the entrained droplets to fall by gravity toward the inlet as the vent stream flows towards the outlet for eventual discharge through the conduit to the atmosphere.

BRIEF DESCRIPTION OF THE DRAWINGS

In the drawings, which illustrate what is currently regarded as the best mode for carrying out the invention.

BRIEF DESCRIPTION OF THE ILLUSTRATED EMBODIMENT

Figure 1:
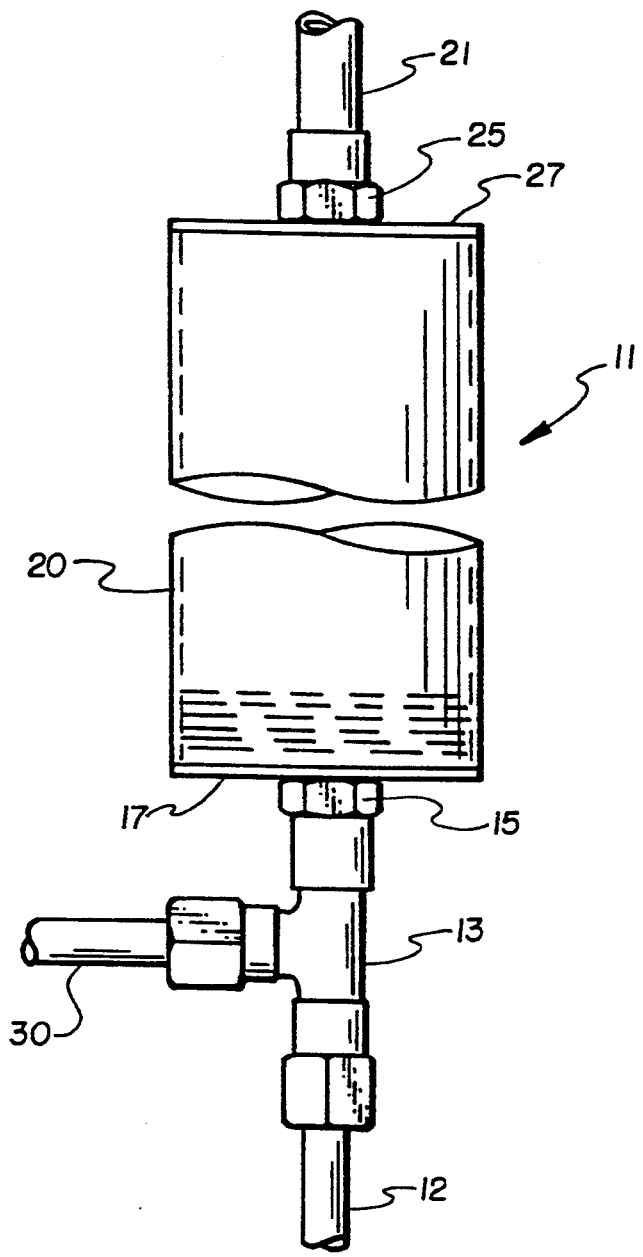
FIG. 1 is a diagrammatic illustration of a generalized form of the invention.
Figure 2:
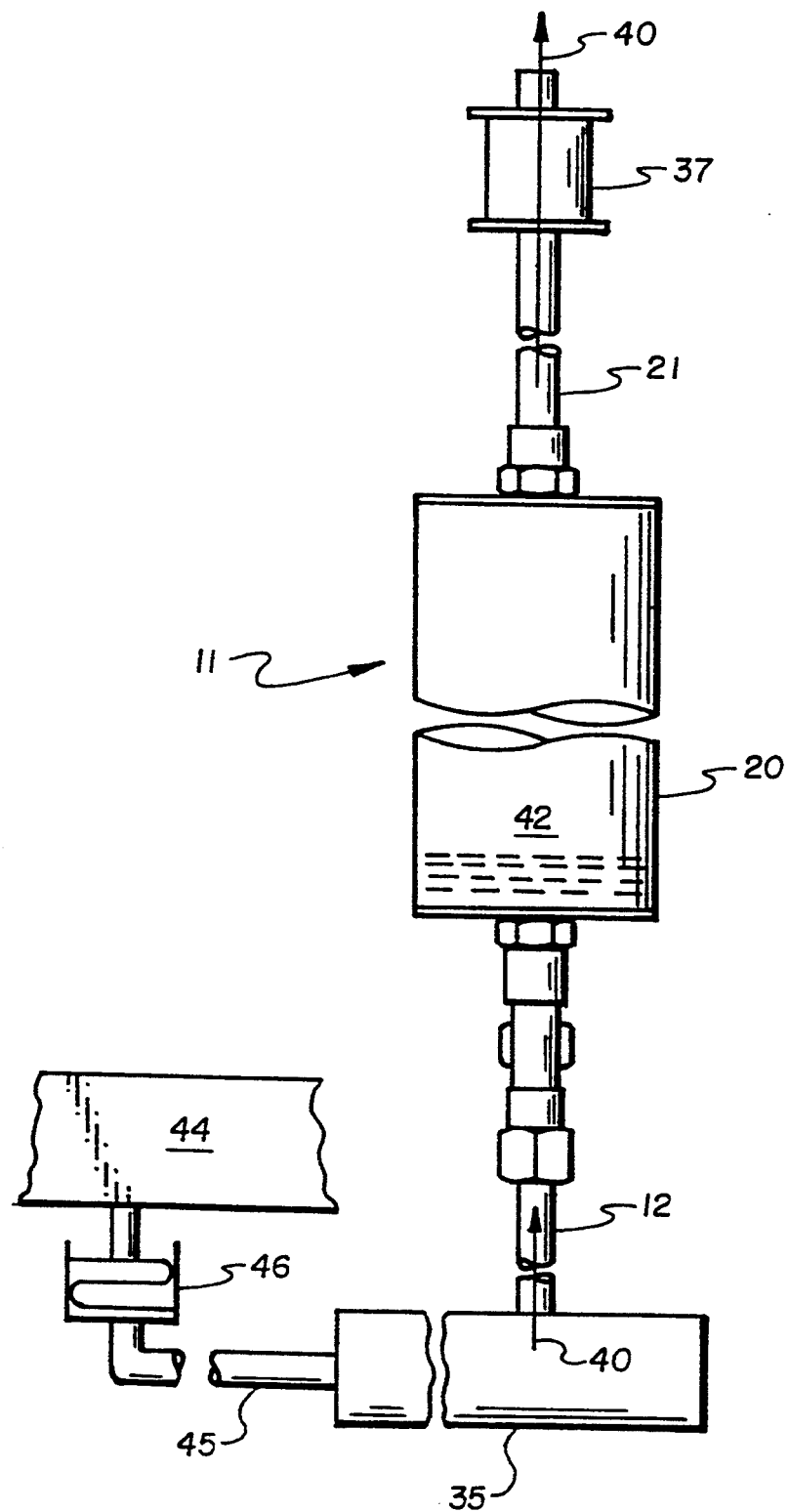
FIG. 2 is an illustration similar to FIG. 1 showing a specific embodiment of the invention.

A condensate separator, designated generally 11, is illustrated in general by FIG. 1, and more specifically by FIG. 2. As illustrated by FIG. 2, a separator 11 of this invention comprises a first conduit 12, connected through appropriate fixtures 13 to an inlet 15 at approximately the center of the bottom 17 of a separator body 20. A second conduit 21 extends from an outlet 25 at approximately the center of the top 27 of the separator body 20. A third conduit 30 constitutes an optional means for introducing saturated vapor to the conduit 12 upstream from the inlet 15. In most instances currently contemplated, however, saturated vapor will be introduced to the conduit 12 directly from a liquid drain receiver tank 35 as shown by FIG. 2.

FIG. 2 illustrates the condensate separator 11 embodied as a portion of a system between a liquid receiver tank 35 and an in-line filter 37. As so positioned, it serves to remove liquid entrained in the vapor stream, designated by the arrow 40, as it rises from the receiver tank 35 to the filter 37. Liquid 42 collects in the lower portion of the separator body and drains back through the supply line (conduit 12) to the tank 35 from which it originates.

Reduced velocity of the vapor stream 40 as it passes through the separator body 20 permits entrained liquid 42 to drop out of the flowing vapor stream 40. The configuration of the condensate separator system 11 allows the pooled liquid 42 to drain by gravity flow countercurrent to the vapor stream 40. In contrast to conventional steam traps, the illustrated system 11 is effective in removing moisture and entrained condensate from a flowing stream 40 of saturated vapor at a temperature close to ambient.

In a typical operation of a chemical sterilizer, such as the HARVEY ® CHEMICLAVE ® sterilizer sold by MDT Corporation of Torrance, Calif., used sterilant leaves the sterilization chamber 44 at a temperature of approximately 130°-135° C. It is then sent to a waste reservoir, such as the liquid receiver tank 35 illustrated, through a conduit 45, configurated in part as a condensing coil 46. The sterilant is cooled, by the coil 46 or by a supplemental coil (not shown) internal the tank 35, to below the vaporization temperature of the claimed sterilant. The sterilant includes various chemical constituents which are not permitted to be discharged into the ambient environment. Most of the chemical agents are condensed and removed in or upstream from the tank 35, and the remaining water-saturated vapor is discharged through the conduit 12 and eventually the filter 37 to the atmosphere. A small amount of chemical sterilant; e.g., formaldehyde, inevitably remains entrained in the flowing vapor stream 40. It is important to recapture this material and to accumulate it in the tank 35 for eventual disposal. It is also important to avoid the phenomenon known as "water hammer" on equipment, such as the filter 37 located downstream from the separator body 20. The illustrated system 11 constitutes a low-cost, effective expedient for accomplishing both of these objectives.

The conduits 12, 21, 45 may be of any convenient cross-sectional area adequate to accommodate the fluid flow requirements of systems in which the condensate separation of the invention may be incorporated. To provide for effective removal of entrained droplets, it is important that the separator body 20 have a cross-section very much greater, typically at least an order of magnitude larger, than the cross-sectional area of the supply conduit 12. All of the illustrated components are most conveniently of circular cross-sectional configuration. A practical sizing range in practice is for the diameter of the separator body 20 to be about 10 to about 20 times the diameter of the conduit 12. The internal volume of the separator body is also significant because it is helpful for the low velocity conditions provided by this component to persist for a significantly long time, as "seen" by the vapor stream 40, to facilitate the desired separation. As a practical matter, the height of the separator body should ordinarily be larger than its diameter, typically by a factor of 2 or more times. In any event, proper sizing of the illustrated components is within the skill of the routineer advised of the objective of the invention and the flow characteristics and other parameters of the specific application at hand. In practice, copper tubing of ¼ to ⅜ inch O.D. is suitable for the conduit 12, and a cylindrical chamber with a diameter of 2 inches and a height of about 4 inches constitutes an adequate separator body 20.

Reference herein to certain details of the illustrated embodiments is not intended to limit the scope of the appended claims which themselves recite those features regarded as important to the invention.

What is claimed:

1. In a condensate separator for use in a sterilizer of the type having means for venting a stream of chemical vapor sterilant through a conduit of a venting system from a sterilizer chamber to atmosphere following a sterilization cycle and including an improved means for capturing droplets of moisture and sterilant from said vent stream, wherein said improved means comprises:
a separator body with an inlet receiving said vent stream and an outlet discharging said vent stream;
said outlet being located vertically higher than said inlet; and means providing a sufficiently lower vent stream velocity within said separator body than is present in said inlet to permit droplets entering said seperator body with a vent stream to fall by gravity towards said inlet as said vent stream flows to said outlet.

2. A condensate separator for use in a sterilizer of the type in which a vent stream of chemical vapor sterilant is passed through a first conduit of a venting system from a sterilizer chamber to the atmosphere following a sterilization cycle, and including an improved means for capturing droplets of moisture and sterilant from said vent stream, said improved means comprising:
a separator body having an inlet connected to said first conduit to receive said vent stream and an outlet connected to said first conduit through which said vent stream is discharged;
said outlet being located vertically higher than said inlet; means providing a sufficiently lower vent stream velocity during passage of said vent stream from said inlet to said outlet through said separator body than is present in said first conduit upstream of said inlet to permit said droplets to fall by gravity into said inlet; and
said inlet being sized to accommodate simultaneous upward flow of said vent stream and downward flow of said droplets therethrough.

3. A condensate separator as in claim 2 further including:
a waste receiver tank having a tank conduit connected to the first conduit upstream of and beneath the separator body, whereby the vent stream is passed through the waste receiver tank into said upstream first conduit and the droplets fall through said inlet of said separator body and through said upstream first conduit into the waste receiver tank.

4. A condensate separator as in claim 3, further including:
a filter connected in the first conduit downstream of the separator body to collect water in the vapor stream discharged from the separator body.

5. A condensate separator as in claim 3, further including:
means supplying used sterilant to the waste receiver tank, said means including an inlet conduit to convey said sterilant, and means to cool the said sterilant.

6. A condensate separator as in claim 5 wherein:
the means to cool the said sterilant is a condensing coil in the inlet conduit.

7. A condensate separator as in claim 4 wherein:
the inlet conduit to the waste receiver tank has means thereon for connection to a sterilizer.

* * * * *